US005928891A

United States Patent [19]
Klier et al.

[11] Patent Number: 5,928,891
[45] Date of Patent: Jul. 27, 1999

[54] **DNA FRAGMENT ENCODING INSECTICIDAL CRYSTAL PROTEINS FROM *BACILLUS THURINGIENSIS***

[75] Inventors: André Klier, Neuilly/Marne; Georges Rapoport, Verrieres Le Buisson; Raymond Dedonder, Chatenay Malabry, all of France

[73] Assignees: Institut Pasteur; Centre National de La Recherche Scientifique, both of Paris, France

[21] Appl. No.: 08/487,644

[22] Filed: Jun. 7, 1995

Related U.S. Application Data

[63] Continuation of application No. 08/329,786, Oct. 27, 1994, abandoned, which is a continuation of application No. 08/070,056, Jun. 1, 1993, abandoned, which is a continuation of application No. 07/888,424, May 27, 1992, abandoned, which is a continuation of application No. 07/729,903, Jul. 15, 1991, abandoned, which is a continuation of application No. 07/376,215, Jul. 5, 1989, abandoned, which is a continuation of application No. 07/031,227, Mar. 30, 1987, abandoned, which is a continuation of application No. 06/488,087, Apr. 25, 1983, abandoned.

[30] Foreign Application Priority Data

Apr. 26, 1982 [FR] France .................................. 82 07201

[51] Int. Cl.[6] ............................ C12N 15/32; C12N 1/21; C12N 15/70; C12N 15/74

[52] U.S. Cl. ........................ 435/69.1; 424/93.2; 424/405; 424/409; 435/71.2; 435/252.3; 435/252.31; 435/252.33; 435/320.1; 435/480; 536/23.71

[58] Field of Search ............................... 435/172.3, 69.1, 435/69.3, 69.7, 252.31, 252.33, 320.1, 71.2, 252.3, 480; 424/93.2, 405, 409; 536/23.71

[56] References Cited

U.S. PATENT DOCUMENTS

| | | | |
|---|---|---|---|
| 3,911,110 | 10/1975 | Smirnoff | 424/93.461 |
| 4,133,716 | 1/1979 | Zamola et al. | 435/71.3 |
| 4,419,450 | 12/1983 | Dean et al. | 435/252.31 |
| 4,448,885 | 5/1984 | Schnepf et al. | 435/252.33 |
| 4,467,036 | 8/1984 | Schnepf et al. | 435/320.1 |
| 4,503,155 | 3/1985 | Miller et al. | 435/252.3 |
| 5,010,001 | 4/1991 | Pollock | 435/69.1 |
| 5,162,206 | 11/1992 | Lovett | 435/69.1 |
| 5,460,963 | 10/1995 | Botterman et al. | 800/279 |
| 5,567,600 | 10/1996 | Adang et al. | 536/23.71 |
| 5,567,862 | 10/1996 | Adang et al. | 800/302 |
| 5,633,446 | 5/1997 | Cornelissen et al. | 800/317.2 |

OTHER PUBLICATIONS

H. Hofte et al, *Microbiological Reviews,* "Insecticidal Crystal Proteins of *Bacillus Thuringiensis*", (1989), 53, pp. 242–255.

(List continued on next page.)

*Primary Examiner*—Johnny F. Railey, II
*Attorney, Agent, or Firm*—Oblon, Spivak, McClelland, Maier & Neustadt, P.C.

[57] ABSTRACT

The invention relates to a vector for transforming microorganisms capable of undergoing sporulation and which contains itself a heterologous insert comprising a DNA sequence coding for at least part of crystal protein, particularly that of *B. thuringensis*. It also concerns the polypeptides expressed by said microorganisms and having insecticidal properties similar to those of crystal protein, the microorganisms themselves, as transformed by this vector and insecticidal composition including either said polypeptide or the microorganism itself.

123 Claims, 1 Drawing Sheet

OTHER PUBLICATIONS

Y. Shibano et al, *Gene,* "Nucleotide Sequence Coding for the Insecticidal Fragment of the *Bacillus Thuringiensis* Crystal Protein", (1985), 34, pp. 243–251.

M. Adang et al, *Gene,* "Characterized Full–Length and Truncated Plasmid Clones of the Crystal Protein of *Bacillus Thuringiensis* Subsp. Kurstaki HD–73 and Their Toxicity to Manduca Sexta", (1985), 36, pp. 289–300.

G. Whal et al, *Proc. Natl. Acad. Sci. USA,* "Efficient Transfer of Large DNA Fragments From Agarose Gels to Diazobenzyloxymethyl–Paper and Rapid Hybridization by Using Dextran Sulfate", (1979), 76, pp. 3683–3687.

H. Wabiko et al, *DNA,* "*Bacillus Thuringiensis* Entomocidal Protoxin Gene Sequence and Gene Product Analysis", (1986), 5, pp. 305–314.

H.E. Schnepf et al, *The Journal of Biological Chemistry,* "The Amino Acid Sequence of a Crystal Protein From *Bacillus Thuringiensis* Deduced From the DNA Base Sequence", (1985), 260, pp. 6264–6272.

H.E. Schnepf et al, *Proc. Natl. Acad. Sci. USA,* "Cloning and Expression of the *Bacillus Thuringiensis* Crystal Protein Gene in *Escherichia Coli*", (1981), 78, pp. 2893–2897.

H.C. Wong et al, *The Journal of Biological Chemistry,* "Transcriptional and Translational Start Sites for the *Bacillus Thuringiensis* Crystal Protein Gene", (1983), 25, pp. 1960–1967.

M. Lilley et al, *Journal of General Microbiology,* "Purification of the Insecticidal Toxin in Crystals of *Bacillus Thuringiensis*", (1980), 118, pp. 1–11.

J. Gonzalez et al, *Proc. Natl. Acad. Sci. USA,* "Transfer of *Bacillus Thuringiensis* Plasmids Coding for δ–Endotoxin Among Strains of *B. Thuringiensis* and *B. Cereus*", (1982), 79, pp. 6951–6955.

D. M. Williams et al, in *Molecular Cloning and Gene Regulation in Bacilli,* "Expression of *E. Coli* TRP Genes Cloned in *B. Subtillis*", A.T. Ganesar et al, Ed, Academic Press, (1982), pp. 91–96.

C.E. Donnelly et al, in *Molecular Cloning and Gene Regulation in Bacilli,* "Genetic Fusion of *E. Coli* Lac Genes to a *B. Subtilis* Promoter", A.T. Ganesar et al, Ed, Academic Press, (1982), pp. 63–72.

P.S. Lovett et al, in *Methods in Enzymology,* "*Bacillus Subtilis* as a Host for Molecular Cloning", R. Wu, Ed, Academic Press, (1979), 68, pp. 342–357.

G. Lee et al, *Molec. Gen. Genet.,* "Nucleotide Sequence of a Promoter Recognized by *Bacillus Subtilis* RNA Polymerase", (1980), 180, pp. 57–65.

A.F. Klier et al, *Eur. J. Blochem,* "Sequential Modifications of DNA–Dependent RNA Polymerase During Sporogenesis in *Bacillus Thuringiensis*", (1973), 36, 317–326.

T. Linn et al, *The Journal of Biological Chemistry,* "RNA Polymerase from Sporulating *Bacillus Subtilis*", (1975), 250, pp. 9256–9261.

Davis et al, *Microbiology,* "Bacterial Physiology", pp. 92.

A. Klier et al, *The EMBO Journal,* "Cloning and Expression of the Crystal Protein Genes from *Bacillus Thuringiensis* Strain Berliner 1715", (1982), 1, pp. 791–799.

Microbiological Reviews, vol. 57, No. 1, pp. 1–33, (Mar. 1993), Jeffrey Errington., "*Bacillus subtilis* Sporulation: Regulation of Gene Expression and Control of Morphogenesis".

Shibano et al, in *Bacillus Molecular Genetics and Biotechnology Applications,* "Complete Structure of an Insecticidal Crystal Protein Gene From *Bacillus Thuringiensis*", (1986), Academic Press, NY, pp. 307–320.

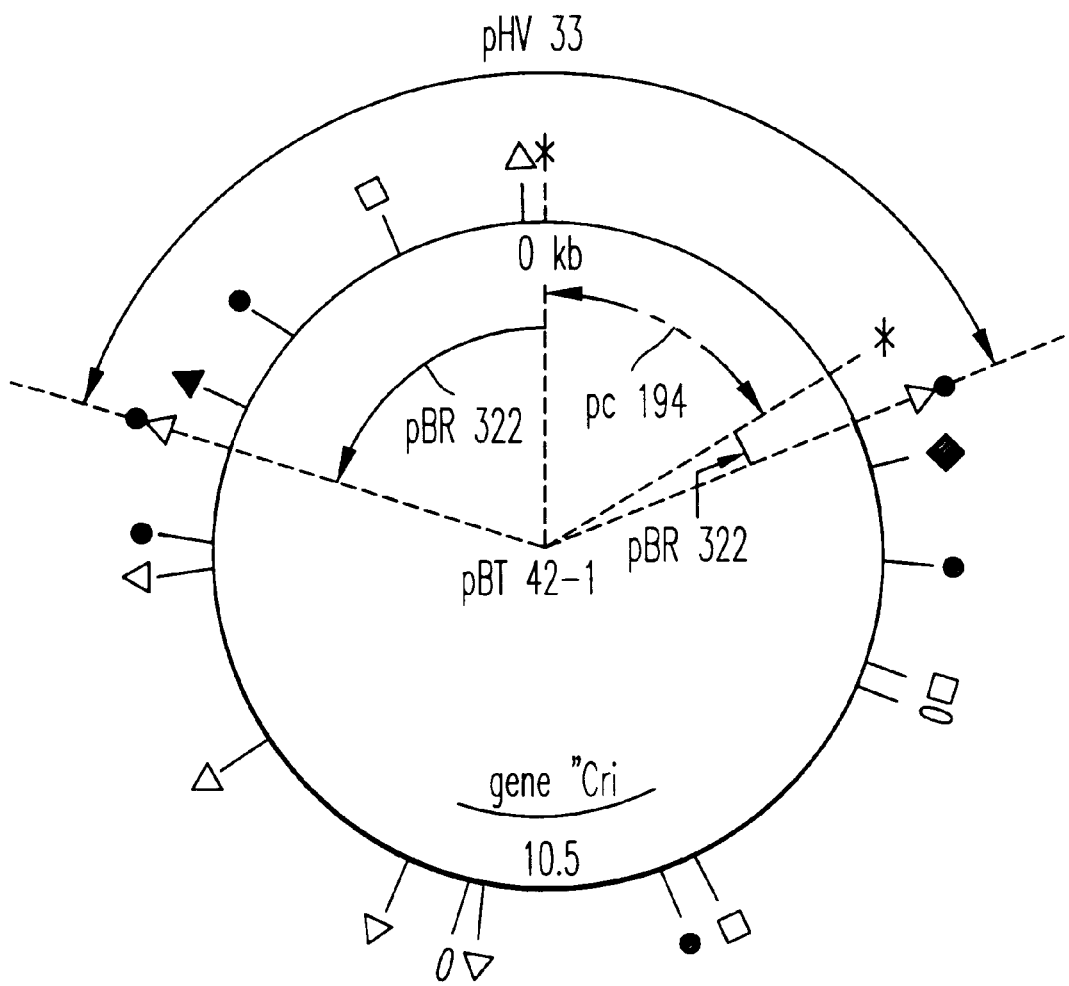

DNA FRAGMENT ENCODING INSECTICIDAL CRYSTAL PROTEINS FROM *BACILLUS THURINGIENSIS*

This is a Continuation of application Ser. No. 08/329,786 filed on Oct. 27, 1994, abandoned, which is a continuation of application Ser. No. 08/070,056, filed Jun. 1, 1993, abandoned, which is a continuation of application Ser. No. 07/888,424, filed May 27, 1992, abandoned, which is a continuation of application Ser. No. 07/729,903, filed Jul. 15, 1991, abandoned, which is a continuation of application Ser. No. 07/376,215, filed Jul. 5, 1989, abandoned, which is a continuation of application Ser. No. 07/031,227, filed Mar. 30, 1987, abandoned, which is a continuation of application Ser. No. 06/488,087, filed Apr. 25, 1983, abandoned.

The invention relates to DNA containing one or several sequences coding for a crystal protein or a polypeptide endowed with insecticidal properties, to microorganisms transformed by such DNA and to insecticidal compositions containing said crystal protein, polypeptide or microorganisms.

By the expression "crystal proteins" is meant intracellular crystallisable or crystallised proteins which are produced by cells of the genus *Bacillus thuringiensis* or the like, when the latter enter into sporulation. These proteins which, in *Bacillus thuringiensis* are formed from a polypeptide having a molecular weight of the order of 130,000 can constitute up to 20 or 30% of bacterial proteins. The toxic properties of these proteins of the crystal with regard to at least certain categories of insects, butterflies, mosquitos and larvae are well known. Crystal proteins of some of the above strains constitute the active principle of insecticidal compositions which are already used in agriculture. This applies particularly to crystal protein extracted from *B. thuringiensis kurstaki*, particularly effective with respect to lepidoptera. Other strains of *B. thuringiensis* are well known. Reference may be made to *Bacillus thuringiensis* sub-type *tolworthi*, *alesti* and *berliner*. The above types of strain also extend to those such as *Bacillus thuringiensis* sub-type *israelensis*, which produce in their sporulation phase a crystal protein effective more particularly against diptera, among which mosquitos and black flies.

Studies already made on various strains of *Bacillus thuringiensis* have shown that according as the type of strain one or more DNA sequences coding for said proteins are carried either by genes or by plasmids, as observed in the frame of the present invention, or by both at the same time, such as in *Bacillus thuringiensis* strain *berliner* 1715.

Within the frame of such structural studies, H. E. SCHNEPF and H. R. WHITELEY succeeded in isolating a fragment bearing a sequence coding for a crystal protein, among the fragments obtained by partial digestion of a plasmid extracted from *B. thuringiensis* sub-type *kurstaki* HD-1, in the presence of the restriction enzyme Sau 3A1 (Proc. Natl. Acad. Sci. USA, vol. 78, No. 5, pp. 2893–2897, 1981). These authors have described the ligation of this fragment into the Bam HI site of the cloning vector pBR 322 and the transformation by the recombinant plasmid obtained (pES1) of a strain of *Escherichia coli* HB 101. The incorporation of the recombinant plasmid in *E. coli* was demonstrated by the expression of the insert contained in pES. 1, into one of the colonies (ES 12) in the form of a polypeptide reacting with antibodies previously formed against the crystal protein extracted from the same initial strain of *B. thuringiensis* and exhibiting the same toxicity with respect to newly hatched caterpillars of particular worm species infesting tobacco plants (caterpillars of the tobacco hornworm). Hence the polypeptide formed possessed indeed properties similar to those of the crystal protein extracted from corresponding strains of *B. thuringiensis*. The amounts produced were very small, compared with those which could be produced by *B. thuringiensis*. According to the hypothesis formulated by the authors, the low production of polypeptide appears as correlated to different regulation pathways of the production of the protein in *B. thuringiensis* and *E. coli*.

Thus an object of the invention is to provide means overcoming such apparent difficulties to at least substantial an extent to achieve expression in a foreign host of a DNA sequence coding for a polypeptide having insecticidal properties similar to those of crystal protein.

Another object of the invention is to provide DNA sequences, particularly vectors, for example of the plasmid type, capable of transforming heterologous microorganisms strains and of inducing more effectively the production of larger amounts of toxic polypeptides having characteristics similar to those of crystal protein, or even other types of toxic polypeptides.

In this respect, a further object of the invention is to provide vectors enabling simultaneous transformations of a same micro-organism, in order to induce the production in or by the latter of several types of toxic polypeptides, including crystal proteins produced by different natural *B. thuringiensis* strains (for example *B. thuringiensis berliner, kurstaki* or *israelensis*) and polypeptide or natural proteins derived from quite distinct natural strains.

Consequently a more particular object of the invention is to provide means, particularly DNA sequences, vectors and micro-organisms, enabling the production of insecticidal compositions containing simultaneously a polypeptide related to crystal protein and distinct insecticidal proteins or polypeptides, hence of chemical compositions with a much wider insecticidal spectrum.

The invention relates also to heterologous strains transformed by DNA containing inserts coding for crystal protein, still more particularly spores of these heterologous micro-organisms.

It is understood that the expression "heterologous", as used herein, aims at showing that the microorganism enabling the expression of a determined gene is distinct from the natural (homologous) microorganism in which said gene in question is normally expressed. This expression is also used herein to denote a DNA sequence (insert) incorporated such as by in vitro genetic recombination, in DNA normally not associated with said insert in nature.

An object of the invention is also to provide specific sequences containing all the genetic information of the crystal protein genes, or of fragments thereof containing at least sufficient genetic information for achieving the expression of a polypeptide possessing nonetheless the toxicity properties required for their possible subsequent use in insecticidal compositions.

The invention arises from the discovery that DNA sequences containing a gene or more generally a sequence coding for a crystal protein or a toxic polypeptide fragment thereof could be expressed also in strains of different microorganisms capable of entering into sporulation, with relatively high yields.

The invention provides in this respect cloning vectors, particularly plasmids, characterised both by their capacity to transform transformable microorganisms capable of entering into sporulation and by the fact that they contain themselves an insert formed from a DNA sequence coding for a polypeptide having toxic properties of the type possessed by crystal protein.

The expression "transformable microorganisms", must be understood as extending to any microorganism heterologous with respect to the sequence contained in the above-said insert, whereby said microorganism is known as having or has acquired the capacity of being transformed by heterologous vectors. Preferred transformable micro-organisms are bacillaceae capable of entering into sporulation, such as *Bacillus subtilis* or *Clostridium perfringens*. In a best mode of the invention the transformable host is a *B. subtilis.*

It goes without saying that the vector must in each case have characteristics and markers,whenever needed,to provide both for the transformation of the transformable micro-organism used and the identification or labelling of the transformed colonies. Among such characteristics, may be mentioned DNA sequences contained in these vectors, which are recognized by the internal regulation mechanisms of the host and their RNA-polymerase, at least those produced in certain phases of the development of these micro-organisms.

As regards more particularly the DNA sequence coding for the above-said polypeptide and which is contained in the above-said insert, it can be characterised by its hybridation capacity with a DNA containing by nature a gene of crystal protein, whether it relates to an original chromosome fragment of the homologous cell or to a plasmid also originating from the homologous cell, or again to a sub-fragmentation sequence obtained from the preceding fragments. Recognition genes which can be used, include cDNA resulting from the reverse transcription of messenger RNA, as results from the transcription of the gene coding for the crystal protein in its natural host. Accordingly the DNA sequence contained in the insert may itself be constituted by a cDNA of such type.

In accordance with a preferred embodiment of the invention, the DNA sequences which can be used for the constitution of the above-said nserts are those which are hybridizable with either the chromosome gene of that of *Bacillus thuringiensis* strain *berliner* 1715, deposited in the National Collection of Microorganism Cultures (C.N.C.M.) under n° I-193, or again with the gene coding for the same protein which is borne by a plasmid of A2 megadaltons contained in said *Bacillus thuringiensis* strain *berliner* 1715. Best modes of those inserts are indicated in the examples hereafter.

Any of the "reference genes" or any DNA fragment containing the gene of the crystal protein, as obtained from said plasmid, if necessary after incorporation thereof into a vector, can be used too. A fragment of particular interest consist of a fragment of 14 kb bounded by Bam HI ends, as is obtained from the above-mentioned 42 Mdal plasmid, and also of a smaller fragment contained within the preceding 14 kb fragment, comprising about 4 kb and bounded by Sst I and Pst I sites.

It is self-evident that it is possible to use as a reference gene any other gene which, when inserted into a suitable vector, particularly a plasmid, as hereafter described, is characterised by its capacity to code for a polypeptide having toxic properties similar to those of crystal protein. In this respect, it is possible to resort, for example, to the pES 1 plasmid mentioned above, manufactured according to the method disclosed in the article of H. E. SCHNEPF and H. P. WHITELEY or to any analogous plasmid.

Naturally these "reference genes", which permit the characterisation of any DNA capable of being employed within the scope of this invention, insofar as they code for a toxic protein of the type indicated, are themselves capable of being inserted in the vectors according to the invention in suitable arrangement to enable the expression of these genes in a suitable host transformed by the plasmid used.

As additional control of the appropriateness of a DNA sequence to code for a toxic protein, after it has been identified by hybridation with a reference gene, such as defined, may also be based on the immunological characterization of the polypeptide whose production would thus have been induced, particularly by reaction with antibodies previously formed against the crystal protein initially obtained from the microorganism from which the DNA sequence used was derived, for example under the conditions described by H. E. SCHNEPF and H. P. WHITELEY or again those which will be recalled below. Another method of control involves the direct action of the polypeptide produced on larvae or insects with regard to which said crystal protein is reputed to be particularly toxic.

As regards the vector itself, in which is incorporated the insert of the genes concerned, it is constituted by any DNA, particularly a vector or cosmid, which is capable of transforming a transformable micro-organism, for example is capable of replicating in *bacillaceae*, such as *Bacillus subtilis.*

A preferred vector is constituted by a plasmid known for its capacity to transform *E. coli*, this plasmid having however been modified by a DNA sequence rendering it suitable to transform other procaryotic organisms adapted to form spores. If need be, the vector is further modified by a DNA sequence enabling the subsequent identification to identify the transformed microorganisms.

In the latter case, the modification consists of the integration into the vector, more particularly in the plasmid, of a selection factor or of a genetic marker enabling the characterization of the transformed colonies.

The selection factor will naturally be chosen according as the nature of the microorganism capable of being transformed by the chosen vector. Preferably when a vector is used which is capable of transforming *E. coli* (for example the pBR 322 plasmid) a selection factor is selected which is capable of being expressed both in gram organisms and in bacillaceae. For example, when the latter is *B. subtilis*, the selection factor consists of the resistance factor to chloramphenicol.

In this regard it is advantageous to use a "bi-functional" plasmid capable of being replicated both in *E. coli* and in *B. subtilis*, such as the revertant recombinant of tetracycline resistant pBR 322 and of the fragment bounded by the Hind III ends of the plasmid pC 194 derived from *Staphylococcus aureus*, inserted in the Hind III site of pBR 322. This bi-functional reactor can be replicated both in *E. coli* and in *B. subtilis*. It is capable of conferring on *E. coli* resistance to ampicillin, to tetracycline and to chloramphenicol, and on *Bacillus subtilis* resistance to chloramphenicol. A strain of *E. coli* SK 15-92 containing this plasmid pHV-33 has been deposited at the C.NC.M. (National Collection of Micro-Organism Cultures" at the Pasteur Institute in Paris, France) under n° I-191. The DNA sequences which subsequently will form the above-said inserts can be inserted particularly in a Pst I site of the above said plasmid, after elongation if required of the terminal ends of the two strands of said insert, through poly(dG) and poly(dC) strands, by means of a terminal deoxynucleotidyl-transferase. It is advantageous, for carrying out this insertion, to use a DNA sequence containing in addition, upstream of the gene coding for crystal protein (or of the DNA sequence hybridizable with the gene of the crystal protein) in the direction of transcription, a sequence containing the promoter of the transcription of the gene of the crystal protein (or of the sequence hybridizable to this gene), under the control of which it is normally placed in natural DNA, normally plasmid, which normally contains it. This promoter will normally be contained in a sequence containing at the most 150 pairs of nucleotides.

Advantageously, the insert is derived from the 14 kb fragment bounded by Bam HI ends, such as obtained from the plasmid of 42 Mdal contained in *Bacillus thuringiensis* strain *berliner* 1715 (C.N.C.M. n° I-193), which contains the whole or a part only of the following sites, in the order which follows:

Bam HI, Pvu II, Eco RI, Eco RI, Eco RI, Sst I, Eco RI, Pvu II, Pst I, Sst I, Pst I, Pvu II, BgI II, Bam HI.

It has been established, particularly in the immunological test which will be shown below and in the toxicity tests with respect to larvae of *Pierris brassicae* that the toxic polypeptide was coded, at least as regards its larger part, by the fragment contained in that (4 kb) bounded by the sites Sst I and Pst I, including therefore the following sites in the order which follows:

Sst I, Eco RI, Pvu II, Pst I ("cri" gene in FIG. 1).

It is self-evident that the invention relates also to vectors containing sequences such as those which have just been specified, the latter having possibly undergone deletions or mutations (resulting, for example, in the disappearance of one or of several of the above-indicated sites) to the extent that these deletions or mutations have not resulted in the loss of the toxic properties of the polypeptides coded by the thus modified nucleotide sequences.

More generally still the invention relates to DNAs, particularly plasmids such as may be obtained by recombination of plasmids extracted from *B. thuringiensis* and from another type of microorganism forming spores, to the extent that the recombinant obtained both contains a sequence coding for a polypeptide having the toxic properties of the crystal protein and possesses the capacity of transforming the other microorganism.

The invention relates also to the heterologous microorganisms themselves transformed by DNA containing a DNA sequence coding for the crystal protein or similar toxic protein and suitably the promoter associated therewith, and possibly too a separate promoter, associated with a factor which is at the same time transcribed and expressed in said microorganism.

The microorganisms of the type concerned are advantageously chosen from among those which contain in their own genome sequences coding for an RNA polymerase and regulation elements enabling the transcription of sporulation genes of these microorganisms, this RNA-polymerase and said regulation elements being also capable of recognising the gene of the crystal protein.

Advantageously the heterologous micro-organism concerned belongs to bacilzlaceae and advantageously is constituted by a *B. subtilis*.

Surprisingly, it has been observed that vectors so modified were capable of efficiently transforming both bacillaceae and *E. coli* (at least as regards the recombinant vectors containing a part of a vector such as pBR 322, whose capacity of transformation of *E. coli* is known), of being transcribed and expressed therein under conditions effective to the point that it is possible to observe with the optical microscope, with a magnification at least equal to 500, particularly of the order of 1,000, inclusions of crystal proteins in cultures of *E. coli* or of bacillaceae, particularly *B. subtilis*, when the latter is in a sporulation phase.

The invention therefore relates also to spores originating from microorganisms containing said plasmid and, if necessary, said crystalline inclusions.

The invention also relates to insecticidal compositions containing the above-said microorganisms, particularly lyophilisates thereof or other forms of preservation, such as spores of said microorganisms when the latter are capable of entering into sporulation, associated if required with solid ingredients suitable for the constitution, when diluted in an aqueous solution, particularly water, of a culture medium favoring the germination of said spores, Additional features of the invention will appear also in the course of the description of the production of transformed microorganisms adapted to produce a toxic protein suitable for the production of insecticidal compositions useful in agriculture.

BRIEF DESCRIPTION OF THE DRAWING

FIG. 1. Vector pBT 42-1.

1) Extraction, from a Plasmid of 42 Mdal of *Bacillus thuringiensis* Strain *berliner* 1715, of a Bam HI Sequence of About 14 kb.

The DNAs of *B. thuringiensis* are recovered from a culture according to the technique of ISCH-HOROWICZ, D. and BURKE J. R. (1981, Nucl. Ac. Res. 9, 2989–2998) or of BIRNBOIM, H. C. and DOLY J. (1979, Nucl. Ac. Res. 7, 1513–1523). The techniques of these authors are however modified by the addition of saccharose in the proportion of 20% by weight to the lysis buffer, to form protoplasts. The suspension of cells was incubated on the water bath at 37° C. for 60 minutes and the formation of protoplasts is followed by phase constrast microscopy. The plasmids were purified in a cesium chloride isopycnic gradient. Electrophoresis of the DNA fractions obtained followed on horizontal plates based on 0.7 or 0.5% agarose gel. The electrophoresis buffer used was constituted by Tris 89 mM, 89 mM boric acid, 2.5 mM $Na_2$ EDTA, pH 8.3 for 16 hours under 3 volts/cm. The plasmids were separated by electrophoresis on gel and the strips displayed by means of ethidium bromide 1 microgram/ml (strips photographed under ultra-violet radiation). The strips corresponding to the plasmid of 42 mMdal were treated with the restriction enzyme Bam HI and the fragments having a size of about 14 kb separated.

2) Construction of the Vector pBT 42-1 Resulting from the Insertion of the Sequence of 14 kb Extracted from the Above-said Plasmid, Itself Obtained from *B. thuringiensis* in the Site Bam HI of pHV 33.

The single figure appended is a restriction map of the final plasmid obtained. It shows, in the recombinant obtained, the original part of pHB 33 (a less thick circular arc) and the above-said fragment 14 kb (thicker circular larc).

The internal circular arcs also show the relative positions in pHV 33 of the DNA sequences respectively originating from pBR 322 (fine continuous circular arc) and from pC 194 (arc in mixed line). The part corresponding to the sequence of pC 194 contains the gene of resistance to chloramphenicol and the promoter associated with it.

The preparation of pBT 42-1 was carried out as follows: 2 micrograms of the Bam HI digest from the plasmids extracted from *B. thuringiensis* and 1 microgram of previously linearised pHV 33 were incubated for 1 hour at 20° C. in a suitable buffer for 16 hours at 8° C., in the presence of 0.25 units of DNA ligase of T4 (of BOEHRINGER), in a volume of 25 microlitres. Aliquot portions (2 microlitres) of the ligation mixture were used to transform the strain of *E. coli* K12 HB 101 (C.N.C.M. no. I-190).

Other aliquots were used to transform *B. subtilis* strain QB 666 (C.N.C.M. I-192), for example, according to the known technique described by DUBNAU, D. DAVIDOFF-ABELSON, R., SCHER, B. and CIRIGLIANO C. (1973, J. Bacteriol. 114, 273–286). The cells containing plasmids resistant to antibiotics were selected on L agar plates supplemented with either ampicilline (100 micrograms/ml), or tetracycline (15 micrograms/ml) or chloramphenicol (5 micrograms/ml).

The transformation ratio of the strain of *B. subtilis* is rather high. Recombinant strains are marked which show the integration of DNA sequence. The transformed strains of *B. subtilis* were cultivated under conditions leading to sporulation, to facilitate the synthesis of a polypeptide having toxic properties similar to those of the crystal protein. The cells of *B. subtilis* in fact transformed by a plasmid containing the gene coding for the crystal protein were shown in fact to contain proteins inclusions having sizes of 0.05 to 0.2 micron (measured by the electron microscope on extracts obtained by sonication of the cells).

In the same way it was observed that the cells of *E. coli* actually transformed by a plasmid containing the gene of the crystal protein produced an inclusion visible in the optical microscope (enlargement 1,000). The crystals showed sizes of the order of 0.05 to 0.5 micron (measured under the above-indicated conditions).

The amounts of protein produced in the form of inclusions reached as well as in *B. subtilis*, 10% of the amount formed in *B. thuringiensis* and in *E. coli*.

3) Detection of Expressed Polypeptides

The cells were ruptured and the proteins and polypeptides formed were collected. The latter were separated in a gel with an exponential gradient of 7.5 to 15% according to the technique of O'FARREL, P. H. (1975, J. Biol. Chem., 250, 4007–4001). The polypeptides were transferred to nitrocellulose filters by the method of BOWEN B. et al (1980, Nucl. Ac. Res., 8, 1–20). The reaction with previously formed antibodies with respect to the crystal protein was carried out by a method of the type described by H. E. SCHNEPF et al, indicated above.

The polypeptides formed are also shown to be particularly toxic with respect to larvae of Pieris brassicae. This has been established by the contacting of newly hatched caterpillars with extracts of transformed *E. coli* and *E. subtilis*, respectively. The medium obtained was spread on small cabbage leaves which were given to the larvae. A considerable proportion of these larvae had perished 18 hours after feeding at room temperature.

In general, the following remarks may also be made with respect to the results obtained by the invention.

It is significant that inserts contained in the plasmids, themselves contained in cells which have produced crystals, detectable by the optical microscope, of toxic polypeptides, were hybridizable with plasmids containing genes coding for the crystal protein, such as obtained from other strains of *B. thuringiensis*, particularly strains *berliner* 22105, *kurstaki* HD1 and *subtoxicus*. It is moreover significant that it was possible to extract a fragment of about 6 kb containing the gene coding for the crystal protein and respectively bounded by ends Sst-1, from these other strains. The molecular weights of the polypeptides synthesised by the above-said cells were found to be of the same order of magnitude as those of the crystal protein.

The cells of *B. subtilis* were found to synthesize the above indicated substantial amounts of toxic polypeptides only when they undergo a sporulation phase, whence the apparent analogy thus established between the RNA-polymerases and the regulation elements enabling the transcription of the sporulation genes in *B. subtilis* and *B. thuringiensis*.

As is self-evident and as emerges moreover already form the foregoing, the invention is in no way limited to those of its types of application and embodiments which have been more especially envisaged; it encompasses on the contrary all modifications.

We claim:

1. A DNA fragment isolated from the 42 megadalton plasmid found in the *Bacillus thuringiensis berliner* 1715 strain deposited with the C.N.C.M. under the accession No. I-193, wherein the fragment contains a gene which encodes an insecticidal crystal protein and the natural promoter upstream of said gene which allows the expression of the crystal protein during the sporulation phase of said Bacillus strain.

2. The DNA fragment of claim 1, which is 14 kilobases bounded by Bam HI restriction site ends and having all or a part of the following restriction sites in the order:

Bam HI, Pvu II, Eco RI, Eco RI, Eco RI, Sst I, Eco RI, Pvu II, Bgl II, Bam HI.

3. The DNA fragment of claim 1, which is 4 kilobases bounded by Sst I and Pst I restriction sites and having the following restriction sites in the order: Sst I, Eco RI, Pvu II, Pst I.

4. A DNA fragment isolated from a strain of *Bacillus thuringiensis*, wherein the fragment contains a gene which encodes an insecticidal crystal protein and the natural promoter upstream of said gene which allows the expression of the crystal protein during the sporulation phase of said Bacillus strain, and wherein the fragment hybridizes with the DNA fragment of claim 1.

5. The DNA fragment of claim 4, which is about 6 kilobases bounded by Sst I restriction sites and is isolated from *Bacillus thuringiensis* strain *berliner* 22105, *kurstaki* HD1, or *subtoxicus*.

6. A cloning vector comprising the DNA fragment of claim 1 as a heterologous insert therein.

7. A cloning vector comprising the DNA fragment of claim 2 as a heterologous insert therein.

8. A cloning vector comprising the DNA fragment of claim 3 as a heterologous insert therein.

9. A cloning vector comprising the DNA fragment of claim 4 as a heterologous insert therein.

10. A cloning vector comprising the DNA fragment of claim 5 as a heterologous insert therein.

11. The cloning vector of claim 6, wherein the vector is a bi-functional plasmid capable of being replicated both in Gram negative bacteria and Bacillaceae microorganisms.

12. The cloning vector of claim 9, wherein the vector is a bi-functional plasmid capable of being replicated both in Gram negative bacteria and Bacillaceae microorganisms.

13. The cloning vector of claim 11, wherein the Bacillaceae is *Bacillus subtilis*.

14. The cloning vector of claim 12, wherein the Bacillaceae is *Bacillus subtilis*.

15. The cloning vector of claim 11, wherein the Gram negative bacteria is *E. coli*.

16. The cloning vector of claim 12, wherein the Gram negative bacteria is *E. coli*.

17. The cloning vector of claim 6, which further comprises a gene encoding a selectable marker.

18. The cloning vector of claim 9, which further comprises a gene encoding a selectable marker.

19. The cloning vector of claim 17, wherein the selectable marker is resistance to chloramphenicol.

20. The cloning vector of claim 18, wherein the selectable marker is resistance to chloramphenicol.

21. A plasmid vector comprising the DNA fragment of claim 1, whereupon transformation of the plasmid vector into a Bacillaceae microorganism capable of sporulation, the transformed microorganism will express said insecticidal crystal protein during the sporulation phase.

22. A plasmid vector comprising the DNA fragment of claim 2, whereupon transformation of the plasmid vector into a Bacillaceae microorganism capable of sporulation, the transformed microorganism will express said insecticidal crystal protein during the sporulation phase.

23. A plasmid vector comprising the DNA fragment of claim 3, whereupon transformation of the plasmid vector into a Bacillaceae microorganism capable of sporulation, the transformed microorganism will express said insecticidal crystal protein during the sporulation phase.

24. A plasmid vector comprising the DNA fragment of claim 4, whereupon transformation of the plasmid vector into a Bacillaceae microorganism capable of sporulation, the transformed microorganism will express said insecticidal crystal protein during the sporulation phase.

25. A plasmid vector comprising the DNA fragment of claim 5, whereupon transformation of the plasmid vector into a Bacillaceae microorganism capable of sporulation, the transformed microorganism will express said insecticidal crystal protein during the sporulation phase.

26. The plasmid vector of claim 21, wherein the vector is a bi-functional plasmid capable of being replicated both in Gram negative bacteria and Bacillaceae microorganisms.

27. The plasmid vector of claim 24, wherein the vector is a bi-functional plasmid capable of being replicated both in Gram negative bacteria and Bacillaceae microorganisms.

28. The plasmid vector of claim 26, wherein the Bacillaceae is *Bacillus subtilis*.

29. The plasmid vector of claim 27, wherein the Bacillaceae is *Bacillus subtilis*.

30. The plasmid vector of claim 26, wherein the Gram negative bacteria is *E. coli*.

31. The plasmid vector of claim 27, wherein the Gram negative bacteria is *E. coli*.

32. The plasmid vector of claim 21, which further comprises a gene encoding a selectable marker.

33. The plasmid vector of claim 24, which further comprises a gene encoding a selectable marker.

34. The plasmid vector of claim 33, wherein the selectable marker is resistance to chloramphenicol.

35. The plasmid vector of claim 33, wherein the selectable marker is resistance to chloramphenicol.

36. The plasmid vector of claim 26, which is pBT 42-1, wherein *E. coli* transformed with said plasmid vector will express the crystal protein as inclusions of toxic crystal polypeptides having sizes of 0.05 to 0.5 microns.

37. A bacterial host cell transformed with the cloning vector of claim 6.

38. A bacterial host cell transformed with the cloning vector of claim 7.

39. A bacterial host cell transformed with the cloning vector of claim 8.

40. A bacterial host cell transformed with the cloning vector of claim 9.

41. A bacterial host cell transformed with the cloning vector of claim 10.

42. A bacterial host cell transformed with the cloning vector of claim 11.

43. A bacterial host cell transformed with the cloning vector of claim 12.

44. A bacterial host cell transformed with the cloning vector of claim 13.

45. A bacterial host cell transformed with the cloning vector of claim 14.

46. A bacterial host cell transformed with the cloning vector of claim 15.

47. A bacterial host cell transformed with the cloning vector of claim 16.

48. A bacterial host cell transformed with the cloning vector of claim 17.

49. A bacterial host cell transformed with the cloning vector of claim 18.

50. A bacterial host cell transformed with the cloning vector of claim 19.

51. A bacterial host cell transformed with the cloning vector of claim 20.

52. A Gram negative host cell transformed with the cloning vector of claim 11.

53. A Gram negative host cell transformed with the cloning vector of claim 12.

54. The transformed host cell of claim 52, which is *E. coli*.

55. The transformed host cell of claim 53, which is *E. coli*.

56. A Bacillaceae microorganism host cell transformed with the cloning vector of claim 11.

57. A Bacillaceae microorganism host cell transformed with the cloning vector of claim 12.

58. The transformed Bacillaceae microorganism of claim 56, which is *Bacillus subtilis*.

59. The transformed Bacillaceae microorganism of claim 57, which is *Bacillus subtilis*.

60. A Bacillaceae microorganism host cell transformed with the plasmid vector of claim 21, wherein said transformed Bacillaceae microorganism expresses said insecticidal crystal protein during the sporulation phase.

61. A Bacillaceae microorganism host cell transformed with the plasmid vector of claim 24, wherein said transformed Bacillaceae microorganism expresses said insecticidal crystal protein during the sporulation phase.

62. A Bacillaceae microorganism host cell transformed with the plasmid vector of claim 26, wherein said transformed Bacillaceae microorganism expresses said insecticidal crystal protein during the sporulation phase.

63. A Bacillaceae microorganism host cell transformed with the plasmid vector of claim 27, wherein said transformed Bacillaceae microorganism expresses said insecticidal crystal protein during the sporulation phase.

64. A *Bacillus subtilis* host cell transformed with the plasmid vector pBT 42-1, wherein the transformed *Bacillus subtilis* will express the crystal protein as inclusions of toxic crystal polypeptides having sizes of 0.05 to 0.2 microns.

65. An *E. coli* host cell transformed with the plasmid vector pBT 42-1, wherein the transformed *E. coli* will express the crystal protein as inclusions of toxic crystal polypeptides having sizes of 0.05 to 0.5 microns.

66. The spores produced from the transformed Bacillaceae microorganism of claim 60 following the sporulation phase.

67. The spores produced from the transformed Bacillaceae microorganism of claim 61 following the sporulation phase.

68. The spores produced from the transformed Bacillaceae microorganism of claim 62 following the sporulation phase.

69. The spores produced from the transformed Bacillaceae microorganism of claim 63 following the sporulation phase.

70. An insecticidal composition which comprises the transformed Bacillaceae microorganism of claim 60 and solid ingredients suitable for constitution of a culture medium.

71. An insecticidal composition which comprises the transformed Bacillaceae microorganism of claim 61 and solid ingredients suitable for constitution of a culture medium.

72. An insecticidal composition which comprises the transformed Bacillaceae microorganism of claim 62 and solid ingredients suitable for constitution of a culture medium.

73. An insecticidal composition which comprises the transformed Bacillaceae microorganism of claim 63 and solid ingredients suitable for constitution of a culture medium.

74. An insecticidal composition which comprises a lyophilizate of the transformed Bacillaceae microorganism of claim 60 and solid ingredients suitable for constitution of a culture medium.

75. An insecticidal composition which comprises a lyophilizate of the transformed Bacillaceae microorganism of claim 61 and solid ingredients suitable for constitution of a culture medium.

76. An insecticidal composition which comprises a lyophilizate of the transformed Bacillaceae microorganism of claim 62 and solid ingredients suitable for constitution of a culture medium.

77. An insecticidal composition which comprises a lyophilizate of the transformed Bacillaceae microorganism of claim 63 and solid ingredients suitable for constitution of a culture medium.

78. An insecticidal composition which comprises a ruptured cell extract of the transformed Bacillaceae microorganism of claim 60 and an appropriate medium for spreading the extract.

79. An insecticidal composition which comprises a ruptured cell extract of the transformed Bacillaceae microorganism of claim 61 and an appropriate medium for spreading the extract.

80. An insecticidal composition which comprises a ruptured cell extract of the transformed Bacillaceae microorganism of claim 62 and an appropriate medium for spreading the extract.

81. An insecticidal composition which comprises a ruptured cell extract of the transformed Bacillaceae microorganism of claim 63 and an appropriate medium for spreading the extract.

82. An insecticidal composition which comprises a lyophilizate of the transformed *Bacillus subtilis* cells of claim 64 and solid ingredients suitable for constitution of a culture medium.

83. An insecticidal composition which comprises a lyophilizate of the transformed *E. coli* cells of claim 65 and solid ingredients suitable for constitution of a culture medium.

84. An insecticidal composition which comprises the spores of claim 66 and a culture medium suitable for germination of said spores.

85. An insecticidal composition which comprises the spores of claim 67 and a culture medium suitable for germination of said spores.

86. An insecticidal composition which comprises the spores of claim 68 and a culture medium suitable for germination of said spores.

87. An insecticidal composition which comprises the spores of claim 69 and a culture medium suitable for germination of said spores.

88. A method of producing an insecticidal crystal protein of *Bacillus thuringiensis* comprising culturing the transformed bacterial host cell of claim 37 and recovering the crystal protein expressed.

89. A method of producing an insecticidal crystal protein of *Bacillus thuringiensis* comprising culturing the transformed bacterial host cell of claim 40 and recovering the crystal protein expressed.

90. A method of producing an insecticidal crystal protein of *Bacillus thuringiensis* comprising culturing the transformed Gram negative host cell of claim 52 and recovering the crystal protein expressed.

91. A method of producing an insecticidal crystal protein of *Bacillus thuringiensis* comprising culturing the transformed Gram negative host cell of claim 53 and recovering the crystal protein expressed.

92. A method of producing an insecticidal crystal protein of *Bacillus thuringiensis* comprising culturing the transformed Gram negative host cell of claim 54 and recovering the crystal protein expressed.

93. A method of producing an insecticidal crystal protein of *Bacillus thuringiensis* comprising culturing the transformed Gram negative host cell of claim 55 and recovering the crystal protein expressed.

94. A method of producing an insecticidal crystal protein of *Bacillus thuringiensis* comprising culturing the transformed Bacillaceae microorganism host cell of claim 56 and recovering the crystal protein expressed.

95. A method of producing an insecticidal crystal protein of *Bacillus thuringiensis* comprising culturing the transformed Bacillaceae microorganism host cell of claim 57 and recovering the crystal protein expressed.

96. A method of producing an insecticidal crystal protein of *Bacillus thuringiensis* comprising culturing the transformed Bacillaceae microorganism host cell of claim 58 and recovering the crystal protein expressed.

97. A method of producing an insecticidal crystal protein of *Bacillus thuringiensis* comprising culturing the transformed Bacillaceae microorganism host cell of claim 59 and recovering the crystal protein expressed.

98. A method of producing an insecticidal crystal protein of *Bacillus thuringiensis* comprising culturing the transformed Bacillaceae microorganism host cell of claim 60 and recovering the crystal protein expressed.

99. A method of producing an insecticidal crystal protein of *Bacillus thuringiensis* comprising culturing the transformed Bacillaceae microorganism host cell of claim 61 and recovering the crystal protein expressed.

100. A method of producing an insecticidal crystal protein of *Bacillus thuringiensis* comprising culturing the transformed Bacillaceae microorganism host cell of claim 62 and recovering the crystal protein expressed.

101. A method of producing an insecticidal crystal protein of *Bacillus thuringiensis* comprising culturing the transformed Bacillaceae microorganism host cell of claim 63 and recovering the crystal protein expressed.

102. A method of producing an insecticidal crystal protein of *Bacillus thuringiensis* comprising culturing the transformed *Bacillus subtilis* of claim 64 and recovering the crystal protein expressed.

103. A method of producing an insecticidal crystal protein of *Bacillus thuringiensis* comprising culturing the transformed *E. coli* of claim 65 and recovering the crystal protein expressed.

104. A DNA fragment which contains a gene which codes for an insecticidal crystal protein of *Bacillus thuringiensis* and a sequence containing regulation elements enabling transcription of the gene encoding the insecticidal crystal protein and enabling the transcription of sporulation genes of Bacillus strains transformed with said DNA fragment.

105. A cloning vector comprising the DNA fragment of claim 104 as a heterologous insert.

106. The cloning vector of claim 105, wherein the vector is a bi-functional plasmid capable of being replicated both in Gram negative bacteria and Bacillaceae microorganisms.

107. A plasmid vector comprising the DNA fragment of claim 104, whereupon transformation of the plasmid vector into a Bacillaceae microorganism capable of sporulation, the transformed microorganism will express said insecticidal crystal protein during the sporulation phase.

108. A bacterial host cell transformed with the cloning vector of claim 105.

109. A Gram negative host cell transformed with the cloning vector of claim 105.

110. The transformed host cell of claim 109, which is *E. coli*.

111. A Bacillaceae microorganism host cell transformed with the cloning vector of claim 105.

112. The transformed Bacillaceae microorganism of claim 111, which is *Bacillus subtilis*.

113. A Bacillaceae microorganism host cell transformed with the plasmid vector of claim 107, wherein said transformed Bacillaceae microorganism expresses said insecticidal crystal protein during the sporulation phase.

114. The spores produced from the transformed Bacillaceae microorganism of claim 113 following the sporulation phase.

115. An insecticidal composition which comprises the transformed bacterial host cell of claim 108 and solid ingredients suitable for constitution of a culture medium.

116. An insecticidal composition which comprises the transformed Gram negative host cell of claim 109 and solid ingredients suitable for constitution of a culture medium.

117. An insecticidal composition which comprises the transformed Bacillaceae microorganism of claim 111 and solid ingredients suitable for constitution of a culture medium.

118. An insecticidal composition which comprises a lyophilizate of the transformed Bacillaceae microorganism of claim 111 and solid ingredients suitable for constitution of a culture medium.

119. An insecticidal composition which comprises a ruptured cell extract of the transformed Bacillaceae microorganism of claim 111 and an appropriate medium for spreading the extract.

120. An insecticidal composition which comprises the spores of claim 114 and a culture medium suitable for germination of said spores.

121. A method of producing an insecticidal crystal protein of *Bacillus thuringiensis* comprising culturing the transformed bacterial host cell of claim 109 and recovering the crystal protein expressed.

122. A method of producing an insecticidal crystal protein of *Bacillus thuringiensis* comprising culturing the transformed Bacillaceae microorganism host cell of claim 111 and recovering the crystal protein expressed.

123. A method of producing an insecticidal crystal protein of *Bacillus thuringiensis* comprising culturing the transformed Bacillaceae microorganism host cell of claim 113 and recovering the crystal protein expressed.

* * * * *